US011578299B2

(12) United States Patent
Kim et al.

(10) Patent No.: US 11,578,299 B2
(45) Date of Patent: Feb. 14, 2023

(54) DEFOAMER FOR FERMENTER, AND MICROORGANISM FERMENTER USING DEFOAMER FOR FERMENTER

(71) Applicant: CJ CHEILJEDANG CORPORATION, Seoul (KR)

(72) Inventors: Ill Hwan Kim, Ulsan (KR); Jae Won Oh, Dangjin-si (KR); Jae Myung Joo, Gunpo-si (KR); Hyun Koo Nam, Suwon-si (KR); Jeong Seok Oh, Seoul (KR); Dong Jo Lee, Incheon (KR); Ki Suhk Han, Gunpo-si (KR); Sang Cheol Joo, Goyang-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 430 days.

(21) Appl. No.: 16/614,195

(22) PCT Filed: May 8, 2018

(86) PCT No.: PCT/KR2018/005263
§ 371 (c)(1),
(2) Date: Nov. 15, 2019

(87) PCT Pub. No.: WO2018/212495
PCT Pub. Date: Nov. 22, 2018

(65) Prior Publication Data
US 2020/0071653 A1    Mar. 5, 2020

(30) Foreign Application Priority Data

May 16, 2017  (KR) ........................ 10-2017-0060487

(51) Int. Cl.
C12M 1/21      (2006.01)
B01D 19/00     (2006.01)
C12M 1/06      (2006.01)

(52) U.S. Cl.
CPC ......... *C12M 41/02* (2013.01); *B01D 19/0052* (2013.01); *C12M 27/02* (2013.01)

(58) Field of Classification Search
CPC .... B01D 19/0052; C12M 27/02; C12M 41/02
See application file for complete search history.

(56) References Cited

U.S. PATENT DOCUMENTS

| 2,750,328 | A | * | 6/1956 | Stimpson | ............... C12M 27/24 261/93 |
| 6,673,599 | B2 | | 1/2004 | Rietschel et al. | |
| 8,785,180 | B2 | * | 7/2014 | Zhang | ............... G02B 21/0016 435/29 |

FOREIGN PATENT DOCUMENTS

| CN | 101948747 A | 1/2011 |
| CN | 202379983 U | 8/2012 |

(Continued)

OTHER PUBLICATIONS

International Search Report dated Aug. 14. 2019, issued to the corresponding International Application No. PCT/KR2018/005263.

(Continued)

*Primary Examiner* — Sean C. Barron
(74) *Attorney, Agent, or Firm* — Stein IP, LLC (57) ABSTRACT

Provided is a defoamer for a fermenter. A defoamer for a fermenter according to an embodiment of the present invention includes: a body (100) having a first hollow (110) at a central portion thereof and having a disk shape; a support (200) having a second hollow (210) connected with the first hollow (110), and extending from an upper surface (120) and a lower surface (130) of the body (100); and a plurality of first vanes (310, 320, 330, 340, 350, 360, 370, and 380) mounted on the lower surface (130) of the body (100).

20 Claims, 9 Drawing Sheets (56) References Cited

FOREIGN PATENT DOCUMENTS

| | | | |
|---|---|---|---|
| CN | 205590638 U | | 9/2016 |
| JP | 1997-131502 A | | 5/1997 |
| JP | H 09-131502 A | | 5/1997 |
| JP | H09131502 A | * | 5/1997 |
| KR | 10-2013-0104935 A | | 9/2013 |
| KR | 10-1392425 B1 | | 5/2014 |
| KR | 10-2014-0099967 A | | 8/2014 |
| KR | 10-2016-0056105 | * | 5/2016 |
| KR | 10-2016-0056105 A | | 5/2016 |
| KR | 10-1822334 B1 | | 1/2018 |
| WO | WO-2013075236 A1 | * | 5/2013 .......... B01F 7/00275 |

OTHER PUBLICATIONS

Extended European Search Report issued by the European Patent Office dated Jan. 14, 2021.
Office Action issued by the Japanese Patent Office dated Oct. 30, 2020.
Chinese Office Action dated Jun. 21, 2022, issued to Chinese Application No. 201880024196.4.

* cited by examiner

Upper surface

Lower surface

| Category | Conventional (DFB) defoamer | | Defoamer according to present invention | |
|---|---|---|---|---|
| | Amount of introduction (Liter) | Lapse time (min) | Amount of introduction (Liter) | Lapse time (min) |
| Start | 15 Liter | 0 min | 15 Liter | 0 min |
| Over Flow (with reference to upper cover of defoamer) | 16.5 Liter | 20 min | 18.5 Liter (123%) | 31 min |
| | | | | |

[FIG. 9]

DEFOAMER FOR FERMENTER, AND MICROORGANISM FERMENTER USING DEFOAMER FOR FERMENTER

TECHNICAL FIELD

The present invention relates to a defoamer used for a fermenter and a fermenter using the defoamer, and more particularly to a defoamer which can effectively remove foams produced in a fermenter, and a fermenter.

BACKGROUND ART

When a biochemical reaction of microorganisms and a fermentation process are used to acquire a fermentation object, foams are formed in fermentation culture media due to introduced oxygen, carbon dioxide produced by fermentation of microorganisms, and the like.

When foams are excessively produced during the fermentation process, the fermentation process is badly influenced and productivity deteriorates.

In order to solve the problem, a foam reduction agent for suppressing production of foams in the fermenter may be introduced, but when the foam reduction agent is excessively introduced, a problem may be caused in the quality of the product.

In order to solve the problems of the excessive introduction of the foam reduction agent, a method for removing foams by installing a mechanical defoamer in the interior of the fermenter has been developed.

Among the conventional defoamers, the disk defoamer is installed in a shaft of an agitator in the interior of a fermenter to remove surrounding foams by using a centrifugal force generated through rotation of the shaft, and has a different effect according to the form of the defoamer.

U.S. Pat. No. 6,673,599 discloses a disk defoamer used for a fermenter, but defoaming efficiency deteriorates due to a small effective defoaming area, defoaming capacity significantly deteriorates when the height of the foams of broth is higher than the height of the defoamer, and the weight of the defoamer is heavy and the structure of the defoamer is very complex so that the defoamer is not suitable for a large-scale fermenter due to a danger of contamination and danger of damage.

DETAILED DESCRIPTION OF THE INVENTION

Technical Problem

An object of the present invention is to provide a defoamer for a fermenter including: a body 100 having a first hollow 110 at a central portion thereof and having a disk shape; a support 200 having a second hollow 210 connected with the first hollow 110, and extending from an upper surface 120 and a lower surface 130 of the body 100; and a plurality of first vanes 310, 320, 330, 340, 350, 360, 370, and 380 mounted on the lower surface 130 of the body 100.

Another object of the present invention is to provide a microorganism fermenter including the defoamer for a fermenter further including: a container in which a fermentation target material is accommodated; a rotary shaft located at a central portion of the container; and one or more agitation blades mounted on the rotary shaft to be rotatable, wherein the body of the defoamer for a fermenter is mounted on the rotary shaft to be located at a height that is not less than the height of the one or more agitation blades located in the container.

Another object of the present invention is to provide a microorganism cultivating method using the microorganism fermenter.

Another object of the present invention is to provide a method for manufacturing a fermentation target object through the microorganism cultivating method.

Technical Solution

An aspect of the present invention provides a defoamer for a fermenter including: a body 100 having a first hollow 110 at a central portion thereof and having a disk shape; a support 200 having a second hollow 210 connected with the first hollow 110, and extending from an upper surface 120 and a lower surface 130 of the body 100; and a plurality of first vanes 310, 320, 330, 340, 350, 360, 370, and 380 mounted on the lower surface 130 of the body 100.

According to an embodiment of the present invention, the plurality of first vanes 310, 320, 330, 340, 350, 360, 370, and 380 may be mounted on the body 100 while being spaced apart from the support 200 by a predetermined interval. Through the structure, foams can be discharged to the outside when the amount of the foams increases abruptly, and the flow of broth (cultivation liquid) (b) can be stabilized.

According to an embodiment of the present invention, any one of the plurality of first vanes 310, 320, 330, 340, 350, 360, 370, and 380 may be mounted to the body 100 while being spaced apart from another adjacent first vane at a uniform interval. Through the structure, the defoaming flow that removes foams may be uniformly generated.

The number of the plurality of first vanes 310, 320, 330, 340, 350, 360, 370, and 380 may be eight. However, the number of the plurality of first vanes 310, 320, 330, 340, 350, 360, 370, and 380 is not limited to eight, and may be any arbitrary number.

According to an embodiment of the present invention, the first vanes 310, 320, 330, 340, 350, 360, 370, and 380 may be formed in a radial direction of the body 100, and each may include an upper end part having a first curvature, which is a curvature that is perpendicular to the body 100, and having a predetermined height, and a lower end part connected to the upper end part, and extending while having a second curvature, which is different from the first curvature. Here, the first curvature that is perpendicular to the body 100 may be a curvature that forms 90 degrees with the body 100, but it is noted that the angle is not limited to 90 degrees. Since the inner side of the plurality of first vanes 310, 320, 330, 340, 350, 360, 370, and 380 also may be welded when the plurality of first vanes 310, 320, 330, 340, 350, 360, 370, and 380 are welded to the body 100 through the structure, the entire circumference of the body 100 may be welded so that contamination due to deposition and residue of broth (b) can be minimized by improving strength and forming a waterproof structure. Since the area in contact with the broth (b) can be increased by the shapes of the plurality of first vanes 310, 320, 330, 340, 350, 360, 370, and 380 including the lower ends of the curved structures, foam removal efficiency can be improved. Since only a uniform amount of broth foams can be divided and suctioned as a curved surface of formed in the lower ends, rotation can be stabilized and defoaming can become uniform. Accordingly, foam (f) removal efficiency can be improved. The length of the lower end can become longer as it goes toward the radial direction of the body 100.

According to an embodiment of the present invention, the plurality of first vanes 310, 320, 330, 340, 350, 360, 370, and 380 may be mounted on the body 100 while being eccentric from a radial direction, of which the center of rotation is the central portion of the body 100, by a predetermined angle (α). The direction of eccentricity of the first vanes may be the rotational direction of the defoamer, and the predetermined angle (α) may be 10 to 45 degrees, in detail, 13 to 20 degrees. The plurality of first vanes are mounted on the body 100 after being made eccentric by a predetermined angle (α) so that the predetermined angle (α) is formed to direct the fluid resistance occurred at a contact part to the outside while defoaming the foams, and, thereby minimizes defoaming resistance and stabilizes the flow of the fluid. Through the structure, the deposition of the broth (b) according to the stay of the broth (b) can be prevented when the defoamer is not operated.

According to an embodiment of the present invention, a plurality of second vanes 410, 420, 430, and 440 mounted on the upper surface 120 of the body 100 may be further provided. The number of the plurality of second vanes may be the same as or smaller than the number of the plurality of first vanes. In detail, the number of the second vanes 410, 420, 430, and 440 may be four. However, the number of the plurality of second vanes is not limited to four, and may be any arbitrary number. Since the second vanes 410, 420, 430, and 440 are mounted to the upper surface 120 of the body 100, the foams (f) can be effectively removed through rotation of the second vanes 410, 420, 430, and 440 even if the foams increase abruptly and the height of the foams becomes higher. Further, since the vanes are mounted both on the upper surface 120 and the lower surface 130 of the defoamer 1000, the area in which the foams (f) are directly defoamed (primary defoaming) can be improved through rotation.

Further, the present invention has a simple structure, can be easily manufactured, and has a light weight as compared with the conventional defoamer.

Considering that the density of the foams on the upper side of the defoamer is lower than the density of the lower side of the defoamer, the number of the plurality of second vanes is made to be smaller than the number of the first vanes, and accordingly, the number of the second vanes can be reduced, and the weight of the defoamer can be reduced. Further, the plurality of second vanes can be formed at the same location as any one of the plurality of first vanes, and accordingly, an effect of stable rotation can be achieved by making the center of weight of the defoamer constant. Further, since the plurality of second vanes 410, 420, 430, and 440 also are mounted on the upper surface 120 of the body 100, foams can be effectively removed even when the defoamer is submerged in the broth (b). The plurality of second vanes also may have the same structure as that of the plurality of first vanes. In detail, the plurality of second vanes may be mounted on the body 100 while being spaced apart from the support 200 by a predetermined interval, any one of the plurality of second vanes may be mounted on the body 100 may be mounted on the body 100 while being spaced apart from another second vane at a uniform interval, and each of the plurality of second vanes may include an upper end formed in a radial direction of the body 100 and formed to have a predetermined height while having a first curvature that is a curvature perpendicular to the body 100, and a lower end connected to the upper end and extending while having a second curvature that is different from the first curvature, and may be mounted on the body 100 while being eccentric from a radial direction, of which the center of rotation is a central portion of the body 100, by a predetermined angle (α). Here, the first curvature that is perpendicular to the body 100 may be a curvature that forms 90 degrees with the body 100, but it is noted that the angle is not limited to 90 degrees. The direction of bending of the second vanes may be the rotational direction of the defoamer, and the predetermined angle (α) may be 10 to 45 degrees, in detail, 13 to 20 degrees. The plurality of second vanes are mounted on the body 100 after being made eccentric by a predetermined angle (α) and thus the predetermined angle (α) is formed such that fluid resistance at a contact part, which is generated when the foams are defoamed is guided to the outside so that the flow of the fluid can be stabilized and the defoaming resistance can be minimized. Through the structure, the deposition of the broth (b) according to the stay of the broth (b) can be prevented when the defoamer is not operated.

According to an embodiment of the present invention, the body 100 may further include a separation/coupling part which separates and couples the defoamer for a fermenter, and the separation/coupling part may be formed in a radial direction of the body.

Further, An aspect of the present invention is to provide a microorganism fermenter including the defoamer for a fermenter further including: a container in which a fermentation target material is accommodated; a rotary shaft located at a central portion of the container; and one or more agitation blades mounted on the rotary shaft to be rotatable, wherein the defoamer for a fermenter is mounted on the rotary shaft to be located at a height that is the same as or higher than the height of the initial broth. The container is a part that accommodates a fermentation target material, and is not restricted as long as the container has a shape that can accommodate the fermentation target material.

The defoamer 1000 for a fermenter is mounted on the rotary body such that the body of the defoamer for a fermenter is located at a height that is the same as or higher than the height of the initial broth. Since the foam (f) floats on the liquid broth (b), the body is mounted on the rotary shaft at a height that is higher than the agitation blades. The defoamer 1000 for a fermenter according to an embodiment of the present invention effectively removes the foams (f) which may badly influence the fermentation process.

Further, an aspect of the present invention provides a microorganism cultivating method using the microorganism fermenter. Since the foams (f) produced by the defoamer 1000 for a fermenter in the fermentation process are effectively removed, the microorganisms in the fermentation broth (b) can fully use the components in the broth (b), and since oxygen in the air can be supplied through the enhancement of the air zone which has no foams at an upper portion of the broth (b), microorganism cultivation efficiency can be improved.

Further, an aspect of the present invention provides a method for manufacturing a fermentation object through the microorganism cultivating method. According to the microorganism cultivating method, the cultivation efficiency of the microorganisms can be improved, and since the activity of the microorganisms also becomes vivid, fermentation objects, such as alcoholic beverages (for example, beer, sake, wine, soju, and whisky) using fermentation of microorganisms, and foods (fermented dairy products) with an excellent quality can be manufactured.

Advantageous Effects of the Invention

According to the present invention, since vanes are mounted on both of the upper surface and the lower surface of the defoamer, a uniform defoaming and contamination preventing structure can be achieved through an increase in a defoaming area, a light weight, lowering of a power load through endowment of an inclination angle of the vanes, a fluidic stability through a structural design of spacing installation with the support, lowering of a secondary defoaming force, and employment of a widthwise curve design.

DESCRIPTION OF THE DRAWINGS

FIGS. 3 to 5 are views illustrating the defoamer for a fermenter of FIG. 2, in which

BEST MODE

1. Defoamer for Fermenter

A defoamer 1000 for a fermenter according to an embodiment of the present invention will be described in detail with reference to the accompanying drawings.

Referring to FIGS. 2 to 5, the defoamer 1000 for a fermenter according to the embodiment of the present invention includes a body 100, a support 200, a plurality of first vanes 310, 320, 330, 340, 350, 360, 370, and 380, and a plurality of second vanes 410, 420, 430, and 440.

The body 100 has a disk shape, and a first hollow 110 is formed at a central portion of the body 100. The first hollow 110 is a part at which the defoamer 1000 for a fermenter is mounted to a rotary shaft of the fermenter 2000, which will be described below.

The support 200 is a part which extends from an upper surface 120 and a lower surface 130 of the body 100. A second hollow 210 connected with the first hollow 110 is formed at a central portion of the support 200.

The first vanes 310, 320, 330, 340, 350, 360, 370, and 380 are parts which rotate together with the defoamer 1000 for a fermenter when the defoamer 1000 is rotated, and remove foams (f) produced by a fermentation process. Broth (b) is accommodated in the interior of the fermenter 2000 in which the defoamer 1000 for a fermenter is installed, and foams (f) are formed by the fermentation of microorganisms. If the defoamer 1000 for a fermenter is rotated, the first vanes 310, 320, 330, 340, 350, 360, 370, and 380 skim a predetermined amount of foams (f) by the rotational volume of the vanes (primary defoaming), and of the skimmed semi-liquid broth (b) is thrown to the outside of the defoamer by a rotational centrifugal force, peripheral foams (f) floating between the interior of the fermenter 2000 and the outer periphery of defoamer 1000 are secondarily uniformly defoamed.

Figure 2:
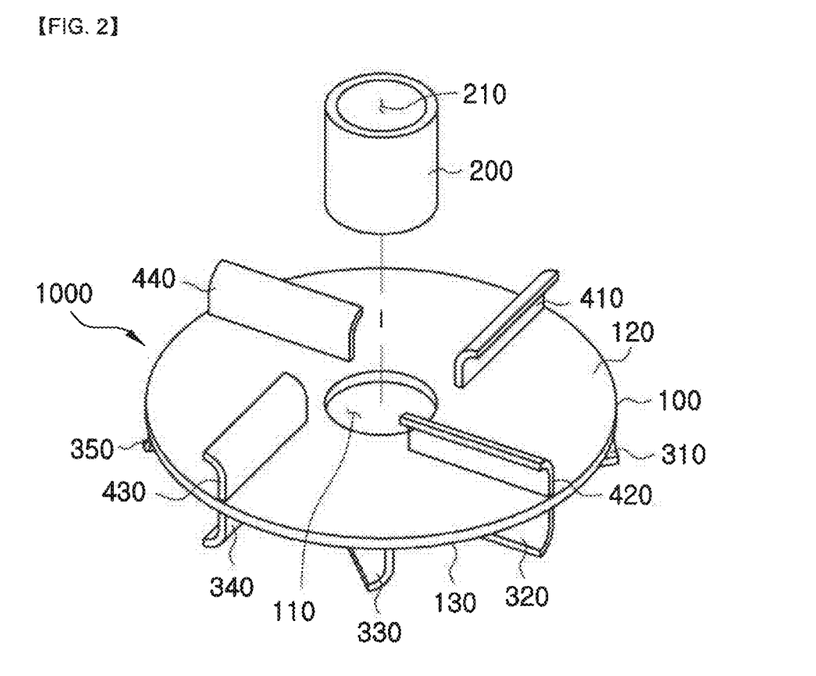
FIG. 2 is an exploded perspective view of a defoamer for a fermenter mounted on the microorganism fermenter of FIG. 1.
Figure 4:
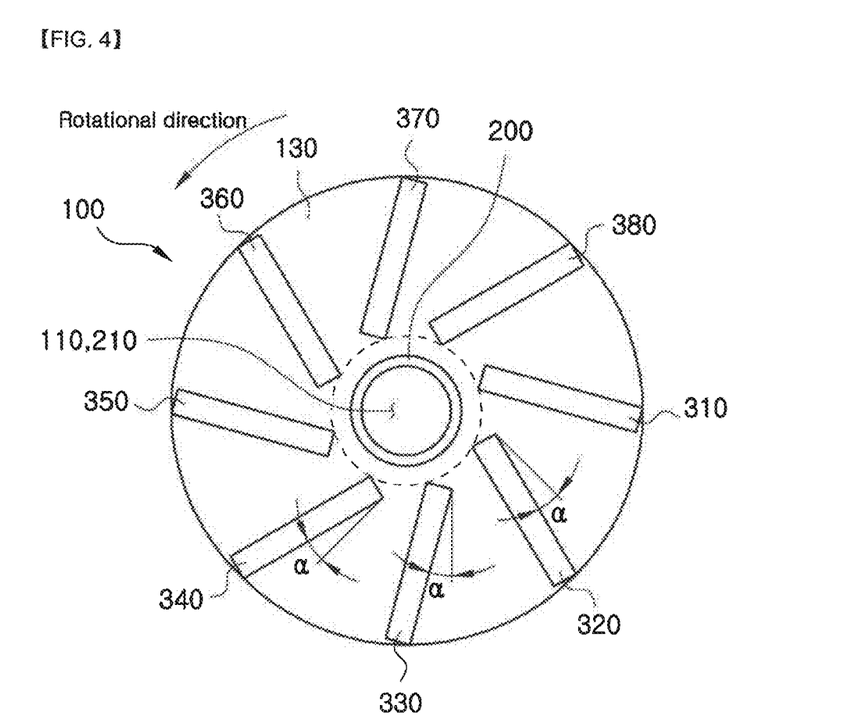
FIG. 4 is a bottom view.
Figure 5:
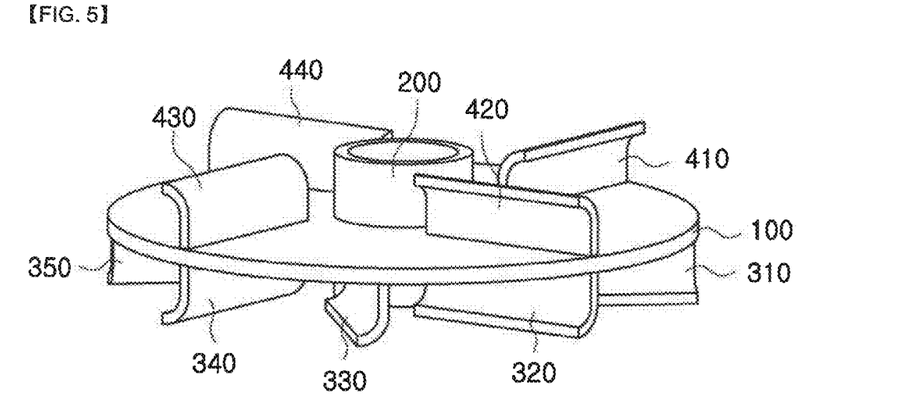
FIG. 5 is a side perspective view.

The first vanes 310, 320, 330, 340, 350, 360, 370, and 380 are mounted on a lower surface 130 of the body 100. Then, any one of the plurality of first vanes 310, 320, 330, 340, 350, 360, 370, and 380 is mounted to the body 100 while being spaced apart from another adjacent first vane at a uniform interval. Accordingly, flows of defoaming which suction and remove a predetermined amount of foams (f) are uniformly produced, and only a predetermined amount of broth foams (f), which are removed, are suctioned and are discharged to the outside in a semi-liquid state. Then, the foams (f) floated around are secondarily defoamed by the centrifugal force.

Figure 3:
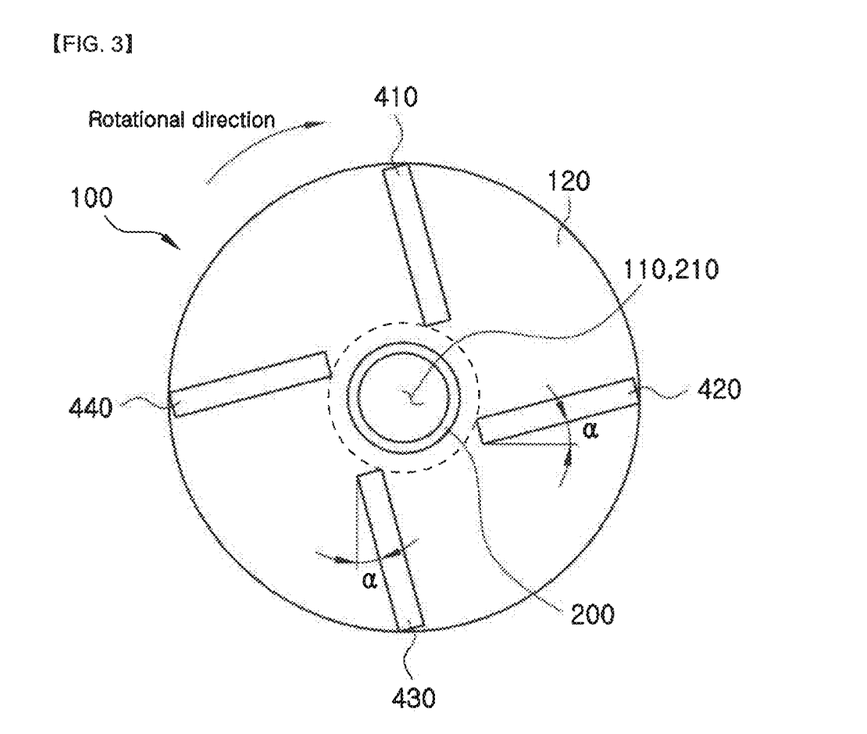
FIG. 3 is a plan view.

The first vanes 310, 320, 330, 340, 350, 360, 370, and 380 are mounted on the body 100 while being spaced apart from the support 200 by a predetermined interval. That is, as illustrated in FIG. 3, a predetermined space is formed between the first vanes 310, 320, 330, 340, 350, 360, 370, and 380 and the support 200.

The first vanes 310, 320, 330, 340, 350, 360, 370, and 380 are formed in a radial direction of the body 100, and each includes an upper end part having a first curvature, which is a curvature that is perpendicular to the body 100, and having a predetermined height, and a lower end part connected to the upper end part, and extending while having a second curvature, which is different from the first curvature.

The first vanes 310, 320, 330, 340, 350, 360, 370, and 380 are mounted on the body 100 to be spaced apart from imaginary lines connected the central portion of the body 100 and outer distal ends of the inner surfaces of the first vanes 310, 320, 330, 340, 350, 360, 370, and 380 by 15 degrees.

Like first vanes, the second vanes 410, 420, 430, and 440 are parts which rotate together with the defoamer 1000 for a fermenter when the defoamer 1000 is rotated, and remove foams (f) produced by a fermentation process. The second vanes 410, 420, 430, and 440 are mounted on the upper surface 120 of the body 100.

The structures of the second vanes 410, 420, 430, and 440 are the same as those of the first vanes. Since the structures of the first vanes have been described above, a detailed description thereof will be omitted.

2. Microorganism Fermenter Including Defoamer for Fermenter

Figure 1:
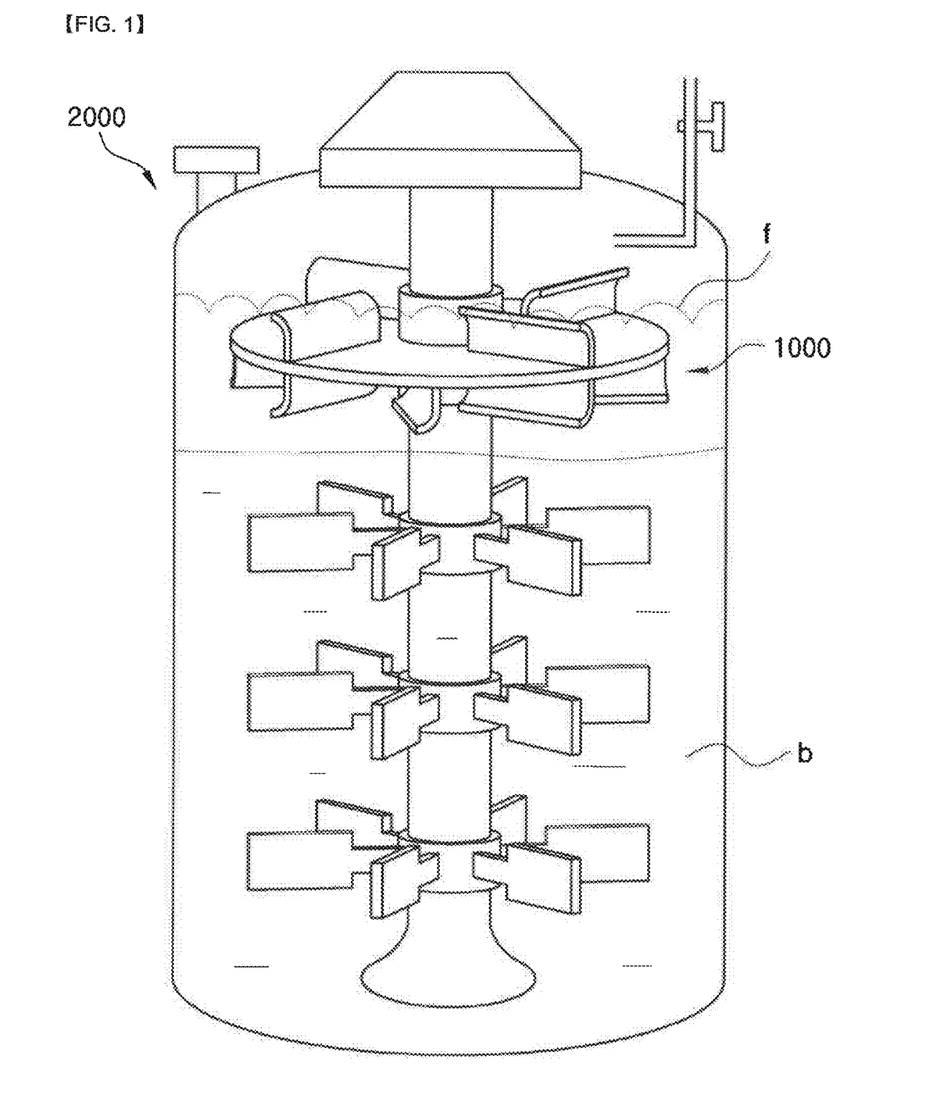
FIG. 1 is a view schematically illustrating a microorganism fermenter according to an embodiment of the present invention.

Referring to FIG. 1, a microorganism fermenter 2000 according to an embodiment of the present invention will be described in detail. FIG. 1 is a view schematically illustrating the microorganism fermenter 2000.

The microorganism fermenter 2000 according to the embodiment of the present invention includes a container, a rotary shaft, one or more agitation blades, and a defoamer 1000 for a fermenter.

The rotary shaft is located at a central portion of the container. Locations at which the agitation blades, which will be described below, and the defoamer 1000 for a fermenter are mounted are provided.

The agitation blades are parts mounted to the rotary shaft. Each of the agitation blades has one or more blades of a predetermined area, and agitates a fermentation target material accommodated in the container through rotation.

3. Verification Experiment

Experiments were carried out by using a disc foam breaker (DFB) defoamer which is an conventional product and the defoamer 1000 for a fermenter according to the embodiment of the present invention to verify the excellency of the defoamer 1000 for a fermenter according to the embodiment of the present invention.

Figure 6:
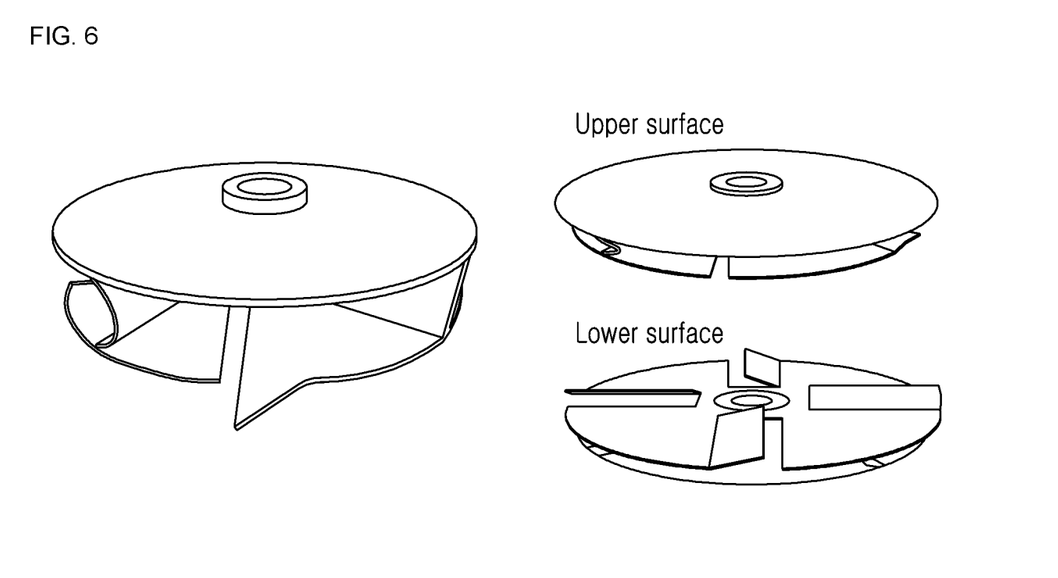
FIG. 6 is a view illustrating an actual appearance of a conventional DFB defoamer.

As illustrated in FIG. 6, the disc foam breaker (DFB) defoamer which is an conventional product is a product in which a vane is not formed on the upper surface thereof and four vanes are formed only on the lower surface thereof.

Figure 7:
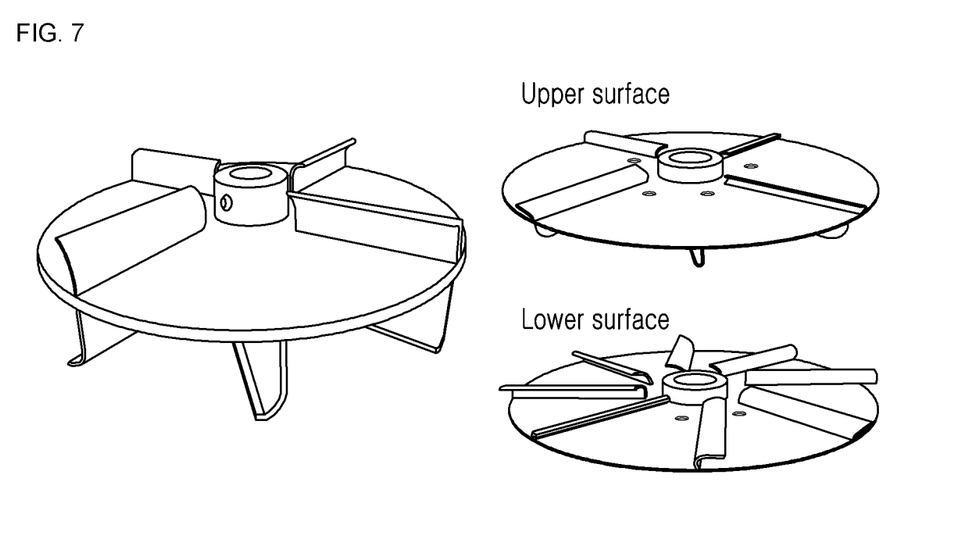
FIG. 7 is a view illustrating an actual appearance of a fermenter according to an embodiment of the present invention.

The defoamer 1000 for a fermenter according to the embodiment of the present invention is as illustrated in FIG. 7.

The foam removal effects were observed after installing the DFB defoamer and the defoamer 1000 for a fermenter according to the embodiment of the present invention at the same locations of fermenters of the capacity of 30 L and introducing broth for lysine production strains of 15 L, and while adding culture media of 0.5 L over time. The same amount of foam reduction agent was added to the initial broth, and saccharide for growth of microorganisms was added while the foam reduction agent is not added.

Figure 8:
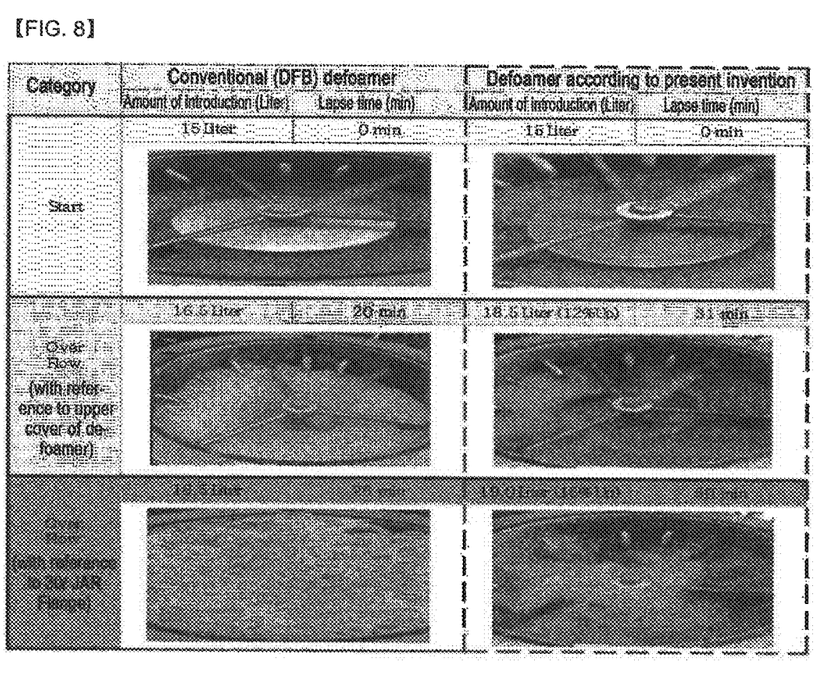
FIG. 8 is a view illustrating an experiment obtained by measuring foam removal efficiency by using the defoamer of FIG. 7.

As illustrated in FIG. 8, the DFB defoamer started to be submerged 20 minutes after the culture media of a total of 1.5 L was additionally added, and the process could not be performed further due to an overflow phenomenon, in which the foams overflows from the fermenter 25 minutes from the culture media of a total of 1.5 L was additionally added.

Meanwhile, the defoamer 1000 for a fermenter according to the embodiment of the present invention started to be submerged 35 minutes after the culture media of a total of 4.0 L was additionally added, but it can be identified that an overflow phenomenon which was severe so that the foams overflow the fermenter did not occur even if the culture media of a total of 4.0 L is additionally introduced.

Figure 9:
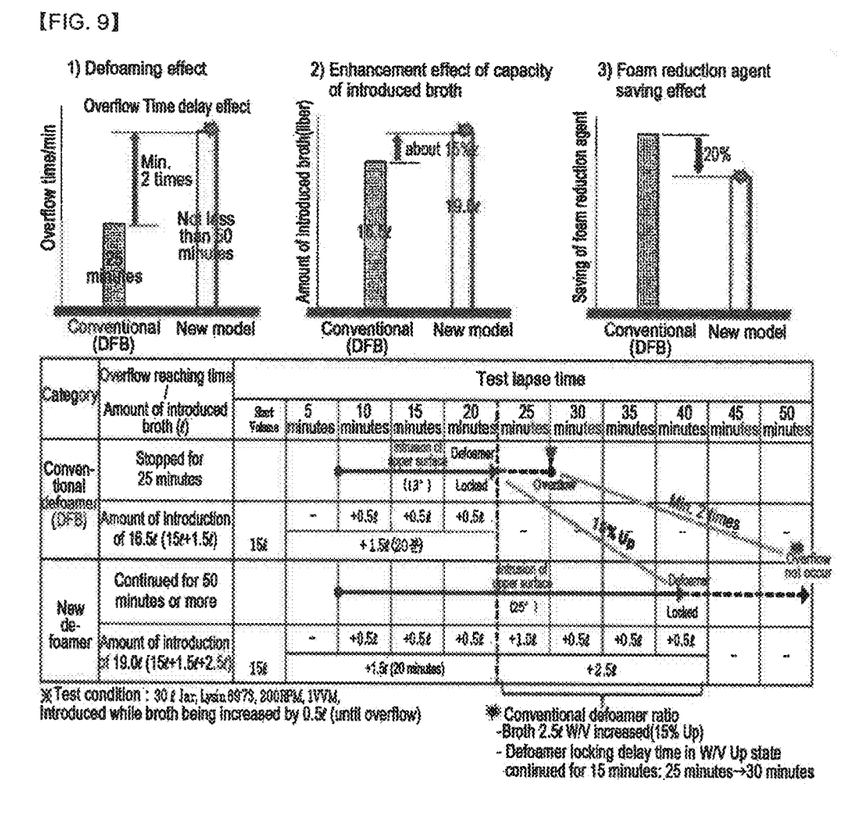
FIG. 9 is a view illustrating an experimental result of FIG. 8.

As illustrated in FIG. 9, it can be identified in the verification experiment of the defoamer 1000 for a fermenter according to the embodiment of the present invention that the overflow time delay effect was more excellent than that of the conventional DFB defoamer by 2 times or more, it can be identified that the capacity of the broth increased by 15% or more, and it can be also identified that the foam reduction agent could be saved by 20%.

Although the embodiments illustrated in the drawings have been described in the specification for reference such that a person skilled in the art can easily understand and realize the present invention, they are merely exemplary and a person skilled in the art can understand that various modifications and equivalent embodiments are also made from the embodiments of the present invention. Therefore, the scope of the present invention should be determined according to the claims.

DESCRIPTION OF REFERENCE NUMERALS

100: body
110: first hollow
120: upper surface
130: lower surface
200: support
210: second hollow
310, 320, 330, 340, 350, 360, 370, 380: first vane
410, 420, 430, 440: second vane
1000: defoamer for a fermenter
2000: microorganism fermenter

The invention claimed is:

1. A defoamer for a fermenter comprising:
    a body having a first hollow at a central portion thereof and having a disk shape;
    a support having a second hollow connected with the first hollow, and extending from an upper surface and a lower surface of the body; and
    a plurality of first vanes mounted on the lower surface of the body,
    wherein the plurality of first vanes comprise an upper end part connected to and extending downwardly from the body, and having a first curvature that is perpendicular to the body; and a lower end part connected to and extending from the upper end part and having a second curvature that is different from the first curvature,
    wherein the body is mounted on a fermenter, the body being configured to be located at a height higher than or equal to the height of initial broth located in a container of the fermenter, and none of radial outer ends of the plurality of first vanes protrudes outwardly with respect to an outer circumferential surface of the body.

2. The defoamer for a fermenter of claim 1, wherein the plurality of first vanes are mounted on the body while being spaced apart from the support by a predetermined interval.

3. The defoamer for a fermenter of claim 1, wherein any one of the plurality of first vanes is mounted to the body while being spaced apart from another adjacent first vane at a uniform interval.

4. The defoamer for a fermenter of claim 1, wherein the plurality of first vanes are formed in a radial direction of the body.

5. The defoamer for a fermenter of claim 1, wherein the plurality of first vanes are mounted on the body while being eccentric from a radial direction, of which the center of rotation is the central portion of the body, by a predetermined angle (α).

6. The defoamer for a fermenter of claim 5, wherein the predetermined angle (α) is 10 to 45 degrees.

7. The defoamer for a fermenter of claim 1, further comprising:
    a plurality of second vanes mounted on the upper surface of the body.

8. The defoamer for a fermenter of claim 1, wherein the body includes a separation/coupling part which separates and couples the defoamer for a fermenter.

9. The defoamer for a fermenter of claim 1, wherein the length of each of lower ends of the plurality of first vanes becomes longer as it goes toward a radial direction of the body.

10. A microorganism fermenter comprising the defoamer for a fermenter of claim 1, the microorganism fermenter comprising:
    a container in which a fermentation target material is accommodated;
    a rotary shaft located at a central portion of the container; and
    one or more agitation blades mounted on the rotary shaft to be rotatable,
    wherein the body of the defoamer for a fermenter is mounted on the rotary shaft to be located at a height that is not less than the height of initial broth located in the container.

11. A microorganism cultivating method using the microorganism fermenter of claim 10.

12. A method for manufacturing a fermentation target object through the microorganism cultivating method of claim 11.

13. A microorganism fermenter comprising the defoamer for a fermenter of claim 2, the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

14. A microorganism fermenter comprising the defoamer for a fermenter of claim 3; the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

15. A microorganism fermenter comprising the defoamer for a fermenter of claim 4, the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

16. A microorganism fermenter comprising the defoamer for a fermenter of claim 5, the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

17. A microorganism fermenter comprising the defoamer for a fermenter of claim 6, the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

18. A microorganism fermenter comprising the defoamer for a fermenter of claim 7, the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

19. A microorganism fermenter comprising the defoamer for a fermenter of claim 8, the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

20. A microorganism fermenter comprising the defoamer for a fermenter of claim 9, the microorganism fermenter comprising:
   a container in which a fermentation target material is accommodated;
   a rotary shaft located at a central portion of the container; and
   one or more agitation blades mounted on the rotary shaft to be rotatable,
   wherein the body of the defoamer for a fermenter is mounted on the rotary shaft to be located at a height that is not less than the height of initial broth located in the container.

* * * * *